(12) United States Patent
Jo et al.

(10) Patent No.: US 10,011,102 B2
(45) Date of Patent: Jul. 3, 2018

(54) SURFACTANT AND METHOD OF MANUFACTURING AN ELECTROWETTING DISPLAY DEVICE USING THE SAME

(71) Applicant: Amazon Technologies, Inc., Seattle, WA (US)

(72) Inventors: Sung-Chan Jo, Yongin-si (KR); Jae-Cheol Park, Pyeongraek-si (KR); Sang-Ji Park, Yongin-si (KR); Hye-Young Park, Seongnam-si (KR); Yiying Jia, Yongin-si (KR); Min-Jeong Oh, Ganghwa-gun (KR); Hee-June Kwak, Yongin-si (KR)

(73) Assignee: Amazon Technologies, Inc., Seattle, WA (US)

( * ) Notice: Subject to any disclaimer, the term of this patent is extended or adjusted under 35 U.S.C. 154(b) by 401 days.

(21) Appl. No.: 14/507,588

(22) Filed: Oct. 6, 2014

(65) Prior Publication Data
US 2015/0029577 A1 Jan. 29, 2015

Related U.S. Application Data (62) Division of application No. 13/605,158, filed on Sep. 6, 2012, now Pat. No. 8,854,719.

(30) Foreign Application Priority Data

Sep. 6, 2011 (KR) .......................... 10-2011-0090020

(51) Int. Cl.
*B01F 3/08* (2006.01)
*G02B 26/00* (2006.01)
(Continued)

(52) U.S. Cl.
CPC .......... *B32B 37/24* (2013.01); *B32B 38/0008* (2013.01); *C07C 323/12* (2013.01);
(Continued)

(58) Field of Classification Search
CPC . B32B 37/24; B32B 38/0008; B32B 2457/20; B32B 2551/00; B32B 2307/40;
(Continued)

(56) References Cited

U.S. PATENT DOCUMENTS 5,171,476 A * 12/1992 Bloodworth ............ C07F 7/184
507/234
5,766,818 A * 6/1998 Smith .................. G03G 9/0806
430/137.17

(Continued)

FOREIGN PATENT DOCUMENTS

KR 1020060120006 A 11/2006
KR 1020080111658 A 12/2008
(Continued)

OTHER PUBLICATIONS

Milton J. Rosen, Surfactans and Interfacial Phenomena (John Whiley & Sons, New York, NY, copyright 1978) pp. 224-250, May 1983.*

(Continued)

*Primary Examiner* — Daniel S Metzmaier
(74) *Attorney, Agent, or Firm* — EIP US LLP (57) ABSTRACT

A surfactant includes a hydrophobic functional group, a hydrophilic functional group and a linker disposed between the hydrophobic functional group and the hydrophilic functional group. The linker is connected to the hydrophobic functional group and the hydrophilic functional group. The linker has a cleavable bond with a bond energy lower than a bond energy of a bond included in the hydrophilic functional group and a bond included in the hydrophobic functional group.

6 Claims, 7 Drawing Sheets

(51) Int. Cl.
*B32B 37/24* (2006.01)
*C07C 323/12* (2006.01)
*B32B 38/00* (2006.01)

(52) U.S. Cl.
CPC ...... *G02B 26/005* (2013.01); *B32B 2037/243* (2013.01); *B32B 2038/0076* (2013.01); *B32B 2307/40* (2013.01); *B32B 2310/0831* (2013.01); *B32B 2457/20* (2013.01); *B32B 2551/00* (2013.01); *G02B 2207/115* (2013.01)

(58) Field of Classification Search
CPC ...... B32B 2310/0831; B32B 2037/243; B32B 2038/0076; G02B 26/005; G02B 2207/115; C07C 323/12
USPC ...................................... 568/22, 62
See application file for complete search history.

(56) References Cited

U.S. PATENT DOCUMENTS

| | | | |
|---|---|---|---|
| 6,306,249 B1 * | 10/2001 | Galante | B01D 17/047 134/22.14 |
| 6,600,076 B1 | 7/2003 | Abbott et al. | |
| 7,980,909 B2 | 7/2011 | Hayes et al. | |
| 8,854,719 B2 * | 10/2014 | Jo | G02B 26/005 359/228 |
| 2003/0027339 A1 * | 2/2003 | Monahan | A61K 48/0025 435/458 |
| 2005/0079145 A1 * | 4/2005 | Constantinides | A61K 8/0291 424/70.11 |
| 2007/0010004 A1 | 1/2007 | Monahan et al. | |
| 2007/0075941 A1 | 4/2007 | Zhou et al. | |
| 2010/0220380 A1 | 9/2010 | Hayes et al. | |

FOREIGN PATENT DOCUMENTS

| WO | WO2005059831 A1 | 6/2005 |
|---|---|---|
| WO | WO2005098797 A2 | 10/2005 |
| WO | WO2009065909 A1 | 5/2009 |
| WO | WO2010133690 A1 | 11/2010 |

OTHER PUBLICATIONS

Hawley's Condensed Chemical Dictionary, (2007), John Wiley & Sons, Inc. Online @ http://onlinelibrary.wiley.com/book/10.1002/9780470114735/titles , pp. 75, 149, 321, 467, 664, 669, 905, 1005, 1164, 1197; (downloaded Mar. 13, 2017), pp. 1-4.*
Office action for U.S. Appl. No. 13/605,158, dated Dec. 27, 2013, Jo et al., "Surfactant and Method of Manufacturing an Electrowetting Display Device Using the Same ", 23 pages.
Korean Office Action dated Dec. 19, 2017 for Korean Application No. 10-2011-0090020.

* cited by examiner

| BOND TYPE | BOND ENERGY (kJ/mol) | BOND TYPE | BOND ENERGY (kJ/mol) |
|---|---|---|---|
| C - C | 607 ± 21 | O - O | 498.36 ± 0.17 |
| C - N | 754.3 ± 10 | O - Si | 799.6 ± 13.4 |
| C - O | 1076.5 ± 0.4 | O - P | 599.1 ± 12.6 |
| C - Si | 451.5 | O - S | 521.7 ± 4.2 |
| C - P | 513.4 ± 8 | S - Si | 623 |
| C - S | 714.1 ± 1.2 | S - P | 444 ± 8 |
| N - N | 945.33 ± 0.59 | S - S | 425.30 |
| N - O | 630.57 ± 0.13 | N - P | 617.1 ± 20.9 |
| N - Si | 470 ± 15 | N - S | 464 ± 21 |

SURFACTANT AND METHOD OF MANUFACTURING AN ELECTROWETTING DISPLAY DEVICE USING THE SAME

CROSS REFERENCE TO RELATED PATENT APPLICATIONS

The present application is a divisional of and claims priority to U.S. patent application Ser. No. 13/605,158, entitled "Surfactant and Method of Manufacturing an Electrowetting Display Device Using the Same," filed Sep. 6, 2012, which claims the benefit of, and priority to Republic of Korea Patent Application No. 10-2011-0090020, entitled "Surfactant and Method of Manufacturing an Electrowetting Display Device Using the Same", filed Sep. 6, 2011, which are incorporated herein by reference in their entirety.

TECHNICAL FIELD

The present disclosure relates to a surfactant, and more particularly, to a surfactant and a method of manufacturing an electrowetting display device using the surfactant.

DISCUSSION OF RELATED ART

An electrowetting display device is a display device using an electrowetting effect. The electrowetting effect refers to an effect in which a contact angle between a conductive hydrophobic fluid and a hydrophobic film disposed under the fluid changes according to the change in a voltage applied to the fluid. Specifically, the smaller the voltage applied to the hydrophobic fluid, the smaller the contact angle between the hydrophobic fluid and the hydrophobic film. Further, the smaller the contact angle, the larger the area of the hydrophobic fluid distributed on the hydrophobic film.

An Electrolyte Level Rising (ELR) technology has been proposed which raises the level of an electrolyte (hydrophilic fluid) disposed in a container to distribute the hydrophilic fluid and a hydrophobic fluid over an entire hydrophobic film between a first substrate and a second substrate of an electrowetting display device. The ELR technology has a process including, for example, the steps of: slantly immersing a first substrate having a hydrophobic film in an electrolyte (hydrophilic fluid) disposed in a container so that the first substrate is inclined with respect to a surface of the fluid, providing a hydrophobic fluid unmixable with the hydrophilic fluid to an area at which the surface of the hydrophilic fluid and the hydrophobic film of the substrate are in contact with each other and raising the height (or level) of the surface of the hydrophilic fluid in the container to distribute the hydrophilic fluid and the hydrophobic fluid over the entire hydrophobic film. However, the ELR technology may require complicated equipment for applying the technology and may also have difficulties in reducing the processing time and in uniformly distributing the fluids on the substrate. Therefore, there may be a need in the art for a manufacturing method which enables the hydrophilic fluid and the hydrophobic fluid to be uniformly distributed on the substrate in a relatively short period of time. Further, there may also be a need in the art for a manufacturing method which requires a relatively simple manufacturing equipment and a low manufacturing cost.

SUMMARY

Example embodiments of the present disclosure provide a way to manufacture an electrowetting display device by using simple equipment.

Example embodiments of the present disclosure provide a way to manufacture an electrowetting display device at a low cost.

Example embodiments of the present disclosure provide a way to manufacture an electrowetting display device in short working time.

Example embodiments of the present disclosure provide a way to manufacture an electrowetting display device in which a hydrophobic fluid is uniformly distributed on a substrate.

In accordance with an example embodiment of the present disclosure, a surfactant is provided. The surfactant includes a hydrophobic functional group, a hydrophilic functional group and a linker disposed between the hydrophobic functional group and the hydrophilic functional group, and the linker is connected to the hydrophobic functional group and the hydrophilic functional group. In addition, the linker has a cleavable bond with a bond energy lower than a bond energy of a bond included in the hydrophilic functional group and a bond included in the hydrophobic functional group.

The hydrophobic functional group has a structure dissolvable by hydrophobic fluid molecules, and the hydrophilic functional group has a structure dissolvable by hydrophilic fluid molecules. The hydrophobic functional group and the hydrophilic functional group include one of a carbon-carbon bond or a carbon-oxygen bond. The cleavable bond has a bond energy lower than a bond energy of the carbon-carbon bond or a bond energy of the carbon-oxygen bond included in the hydrophobic functional group and the hydrophilic functional group, and the cleavable bond is configured to be broken by absorbing an energy of no less than the bond energy of the carbon-carbon bond or bond energy of the carbon-oxygen bond included in the hydrophobic functional group and the hydrophilic functional group.

The cleavable bond has a bond energy which is no greater than about 600 kJ/mol. The cleavable bond may have a bond selected from the group consisting of a carbon-silicon (C—Si) bond, a carbon-phosphorus (C—P) bond, a nitrogen-silicon (N—Si) bond, a nitrogen-sulfur (N—S) bond, an oxygen-oxygen (O—O) bond, an oxygen-sulfur (O—S) bond, a sulfur-phosphorus (S—P) bond, a sulfur-sulfur (S—S) bond, and combinations thereof.

The hydrophobic functional group may be a functional group of a hydrocarbon having ten or more carbons, the hydrophilic functional group may include an ether functional group, and the cleavable bond may be a sulfur-sulfur (S—S) bond.

The surfactant may be a 2-[(Methoxyethoxy)ethoxy]ethyl decyl disulfide.

The surfactant may be manufactured from an alcohol, which is the first starting material, and a thiol, which is the second starting material.

The hydrophobic functional group may be an alkane functional group having ten or more carbons.

The cleavable bond of the surfactant may have a bond selected from the group consisting of a carbon-silicon (C—Si) bond, a carbon-phosphorus (C—P) bond, a nitrogen-silicon (N—Si) bond, a nitrogen-sulfur (N—S) bond, an oxygen-oxygen (O—O) bond, an oxygen-sulfur (O—S) bond, a sulfur-phosphorus (S—P) bond, a sulfur-sulfur (S—S) bond, and combinations thereof.

The hydrophilic functional group may include an ether bond.

The cleavable bond may be broken by an energy supplied from outside of the surfactant and the energy may be provided by ultraviolet rays, heat, or a combination thereof.

The cleavable bond may be broken by an energy lower than bond energies of bonds included in the hydrophobic functional groups and bonds included in the hydrophilic functional groups.

In accordance with an example embodiment of the present disclosure, an electrowetting display device is provided. The electrowetting display device includes a first substrate, a pixel electrode disposed on the first substrate, a hydrophobic film disposed on the pixel electrode, a hydrophobic fluid disposed on an area of the hydrophobic film, and the hydrophobic fluid is configured to move on the hydrophobic film in response to a voltage applied to the pixel electrode, a hydrophilic fluid disposed on the hydrophobic fluid and a second substrate disposed on the hydrophilic fluid and spaced apart from the hydrophobic film. The hydrophobic fluid includes molecules including hydrophobic functional groups of a cleavable surfactant and the hydrophilic fluid includes molecules including hydrophilic functional groups of the cleavable surfactant.

The surfactant includes a hydrophobic functional group, a hydrophilic functional group, and a linker interconnecting the hydrophobic functional group and the hydrophilic functional group. The linker has a cleavable bond, and the hydrophobic fluid or the hydrophilic fluid may include an element participating in the cleavable bond.

The cleavable surfactant may have a bond selected from the group consisting of a carbon-silicon (C—Si) bond, a carbon-phosphorus (C—P) bond, a nitrogen-silicon (N—Si) bond, a nitrogen-sulfur (N—S) bond, an oxygen-oxygen (O—O) bond, an oxygen-sulfur (O—S) bond, a sulfur-phosphorus (S—P) bond, a sulfur-sulfur (S—S) bond, and combinations thereof.

The cleavable bond may be a sulfur-sulfur (S—S) bond and the hydrophobic fluid or the hydrophilic fluid may include thiol molecules.

The hydrophobic fluid may include a saturated hydrocarbon having at least ten carbon atoms, the hydrophilic fluid may include ethylene glycol and glycerin, the hydrophobic functional group may be a functional group of a hydrocarbon having ten or more carbons, and the hydrophilic functional group may include a functional group including an ether bond.

The surfactant may further include a linker interconnecting the hydrophobic functional group and the hydrophilic functional group, and the linker may have a cleavable bond selected from the group consisting of a carbon-silicon (C—Si) bond, a carbon-phosphorus (C—P) bond, a nitrogen-silicon (N—Si) bond, a nitrogen-sulfur (N—S) bond, an oxygen-oxygen (O—O) bond, an oxygen-sulfur (O—S) bond, a sulfur-phosphorus (S—P) bond, a sulfur-sulfur (S—S) bond, and combinations thereof.

The cleavable bond may be a sulfur-sulfur (S—S) bond and the hydrophobic fluid or the hydrophilic fluid may include thiol molecules.

In accordance with an example embodiment of the present disclosure, a method of manufacturing an electrowetting display device is provided. The method includes providing a first substrate including a first base substrate having a plurality of pixel electrodes formed on the first base substrate, a hydrophobic film formed on the plurality of pixel electrodes, and at least one sealing member formed at an edge of the first substrate, mixing a hydrophobic fluid, a hydrophilic fluid, and a cleavable surfactant with each other to form an emulsion, wherein the cleavable surfactant includes a hydrophobic functional group, a hydrophilic functional group and a linker disposed between the hydrophobic functional group and the hydrophilic functional group, and wherein the linker is connected to the hydrophobic functional group and the hydrophilic functional group. The linker has a cleavable bond with a bond energy lower than a bond energy of a bond included in the hydrophilic functional group and a bond included in the hydrophobic functional group. The method further includes applying the emulsion on the first substrate, applying at least one of ultraviolet rays or heat on the emulsion applied on the first substrate to separate the hydrophobic fluid and the hydrophilic fluid from each other and disposing a second substrate on the sealing members of the first substrate.

A substantially identical amount of hydrophobic fluid may be distributed in each of the pixel electrodes.

A width of a pixel disposed on the first substrate in an area in which the emulsion is disposed may be greater than a width of a pixel disposed on another area of the first substrate in which the emulsion is not disposed. The emulsion may be dispensed onto the first substrate through a nozzle of a dispenser as a droplet, the emulsion droplet may have a width in a direction parallel to the first substrate before the emulsion is dropped onto the substrate after being discharged out of the nozzle, and the width of at least one of the pixels disposed on the first substrate may be smaller than the width of the emulsion droplet.

The emulsion droplet becomes a dispensed emulsion when the emulsion droplet has been dispensed onto the first substrate, and the dispensed emulsion may have a width greater than the width of at least one of the pixels disposed on the first substrate.

The width of the dispensed emulsion may not be greater than ten times the width of at least one of the pixels disposed on the first substrate.

The emulsion may be dispensed onto the first substrate after becoming an emulsion droplet formed by the nozzle of the dispenser, the emulsion droplet becomes a dispensed emulsion when the emulsion droplet has been dispensed onto the first substrate, and one dispensed emulsion may overlap an adjacent dispensed emulsion.

The emulsion may be formed by mixing the hydrophobic fluid, the hydrophilic fluid, and the cleavable surfactant within a container.

The cleavable surfactant may include a hydrophobic functional group, a hydrophilic functional group, and a linker interconnecting the hydrophobic functional group and the hydrophilic functional group and having a cleavable bond, and the at least one of the ultraviolet rays or heat applied on the emulsion may have an intensity capable of breaking the cleavable bond earlier than bonds of the hydrophilic functional group and the hydrophobic functional group.

In accordance with an example embodiment of the present disclosure, a method of manufacturing an electrowetting display device is provided. The method includes providing a first substrate including a first base substrate having a plurality of pixel electrodes formed on the first base substrate and a hydrophobic film formed on the plurality of pixel electrodes, mixing a hydrophobic fluid, a hydrophilic fluid, and a surfactant having a linker with each other to form an emulsion including a micelle in which a hydrophobic functional group of the surfactant is bonded to a molecule of the hydrophobic fluid, a hydrophilic functional group of the surfactant is bonded to a hydrophilic molecule of the hydrophilic fluid, and the linker of the surfactant has a cleavable bond that interconnects the hydrophobic functional group and the hydrophilic functional group to each other, wherein the hydrophobic functional group and the hydrophilic functional group include at least one of a carbon-carbon bond or a carbon-oxygen bond. The cleavable bond has a bond energy lower than a bond energy of the at least one of a carbon-carbon bond or a carbon-oxygen bond included in the hydrophobic functional group and the hydrophilic functional group.

In addition, the method further includes applying the emulsion on the first substrate, applying a form of energy to the emulsion to break the cleavable bond of the linker of the surfactant and to separate the hydrophobic fluid and the hydrophilic fluid from each other such that the separated hydrophobic fluid and the separated hydrophilic fluid are unmixable with each other and disposing a second substrate on the first substrate.

By using the separable surfactants according to example embodiments of the present disclosure, it is possible to uniformly distribute the hydrophobic fluid over the entire display device. Further, it is possible to manufacture an electrowetting display device by simple manufacturing facilities, with low manufacturing costs, and in a short manufacturing time.

BRIEF DESCRIPTION OF THE DRAWINGS

Example embodiments of the present disclosure can be understood in more detail from the following detailed description taken in conjunction with the accompanying drawings, in which.

DETAILED DESCRIPTION

Hereinafter, example embodiments of the present disclosure will be described with reference to the accompanying drawings. In the following description, the same elements will be designated by the same reference numerals although they are shown in different drawings. Further, various specific definitions found in the following description, such as specific numeral values are provided only to help general understanding of example embodiments of the present disclosure, and it is apparent to those skilled in the art that example embodiments of the present disclosure can be implemented without such definitions.

It will be understood that when an element or layer is referred to as being "on", "connected to" or "coupled to" another element or layer, it can be directly on, connected or coupled to the other element or layer or intervening elements or layers may be present.

As used herein, the singular forms, "a", "an" and "the" are intended to include the plural forms as well, unless the context clearly indicates otherwise. As used herein, the term "and/or" includes any and all combinations of one or more of the associated listed items.

Figure 1A:
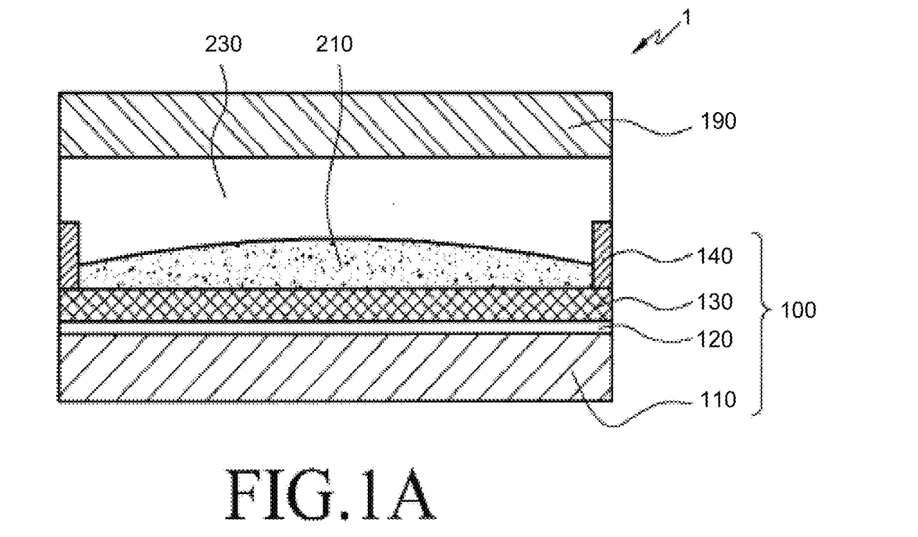
FIGS. 1A and 1B are rough enlarged sectional views of one pixel of an electrowetting display device.
Figure 1B:
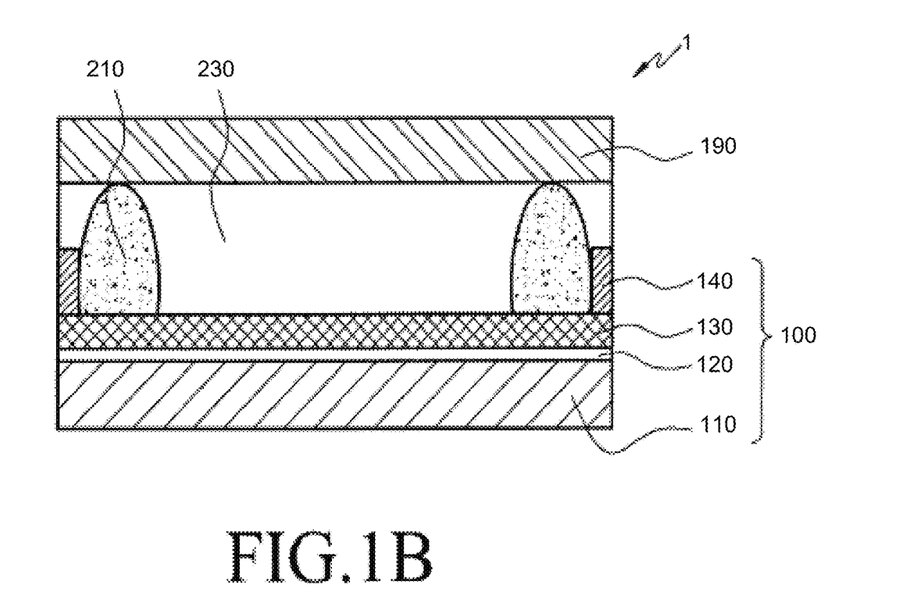

FIGS. 1A and 1B are rough enlarged sectional views of one pixel of an electrowetting display device. The electrowetting display device 1 includes, for example, a first substrate 100, a hydrophobic fluid 210 disposed on the first substrate 100, a hydrophilic fluid 230 disposed on the hydrophobic fluid 210 and unmixable with the hydrophobic fluid 210, and a second substrate 190. The hydrophobic fluid 210 and the hydrophilic fluid 230 are interposed between the first substrate 100 and the second substrate 190. The first substrate 100 may include, for example, a first base substrate 110, a pixel electrode 120 formed on the first base substrate 110, and a hydrophobic film 130 formed on the pixel electrode 120. For example, hydrophobic banks 140 limiting the movement of the hydrophobic fluid 210 are formed on parts of the hydrophobic film 130.

The hydrophobic fluid 210 is, for example, a fluid containing a dye of a predetermined color and is distributed over the entire hydrophobic film 130 as shown in FIG. 1A when no voltage is applied to the pixel electrode 120. For example, when the hydrophobic fluid 210 includes a black dye, the light having entered into the pixel from the exterior of the first substrate 100 cannot pass through the hydrophobic fluid 210, and the pixel thus looks black. When a voltage is applied to the pixel electrode 120, the hydrophobic fluid 210 moves toward the hydrophilic banks 140 in proportion to the voltage applied to the pixel electrode 120 as shown in FIG. 1B. In this event, the area of the black hydrophobic fluid 210 distributed on the hydrophobic film 130 changes according to a change in the value of the voltage applied to the pixel electrode 120. As the contrast level of the display device 1 is in proportion to an exposed area of the hydrophobic film 130, the display device 1 displays a predetermined image.

The first base substrate 110 and the second substrate 190 may be, for example, a flexible substrate or a rigid substrate. For example, the first base substrate 110 and the second substrate 190 may include flexible substrates made of glass, plastic, or a glass fiber reinforced plastic (FRP).

In addition, the pixel electrode 120 may include, for example, a transparent conductive material such as ITO (indium tin oxide), IZO (indium zinc oxide), aluminum zinc oxide (AZO), or cadmium tin oxide (CTO). Alternatively, the pixel electrode 120 may include, for example, a reflective electric conductor such as aluminum (Al), gold (Au), silver (Ag), copper (Cu), iron (Fe), titanium (Ti), tantalum (Ta), molybdenum (Mo), rubidium (Rb), tungsten (W), and alloys, or combinations thereof.

Moreover, the hydrophobic film 130 may include, for example, amorphous fluoropolymers such as copolymers of tetrafluoroethylene (TFE) and perfluoro-2,2 dimethyl 1,3 dioxide (PDD), sold under the brand name TEFLON® AF 1600 which is a registered trademark of the E.I. DuPont de Nemours and Company Corporation, 101 West 10th St., Wilmington, Del. 19898. Alternatively, other low surface energy polymers such as, for example, parylene may be used to form the hydrophobic film.

The hydrophilic banks 140 may include, for example, a positive photoresist, a negative photoresist, a photoset resin or a thermoset resin.

For example, according to characteristics of example embodiments of the present disclosure, a hydrophobic fluid 210 and a hydrophilic fluid 230, which are originally not mixed with each other, are mixed with each other to become an emulsion by a surfactant. A molecule of the surfactant is expressed by, for example, a general formula R(Pho)-L-R (Phi), which includes a hydrophobic functional group R(Pho) and a hydrophilic functional group R(Phi) having structures, which can be mixed well with the hydrophobic fluid 210 and the hydrophilic fluid 230, and a linker L, which interconnects the hydrophobic functional group R(Pho) and the hydrophilic functional group R(Phi) to each other. In addition, the linker L has a cleavable bond of a low bond energy. It is noted that reference characters R(Pho) and 310 are used inter-changably throughout to refer to the hydrophobic functional group of the surfactant molecule and reference characters R(Phi) and 320 are used inter-changably throughout to refer to the hydrophilic functional group of the surfactant molecule.

After the emulsion is applied onto a substrate, the cleavable bonds of the surfactant molecule included in the emulsion are broken by absorbing an energy, such as, for example, light or heat, and the functional groups of the surfactant molecules are then mixed with hydrophobic 210 and hydrophilic 230 fluids. Therefore, it is possible to produce an electrowetting display device including hydrophobic and hydrophilic fluids unmixable with each other.

Figure 2:
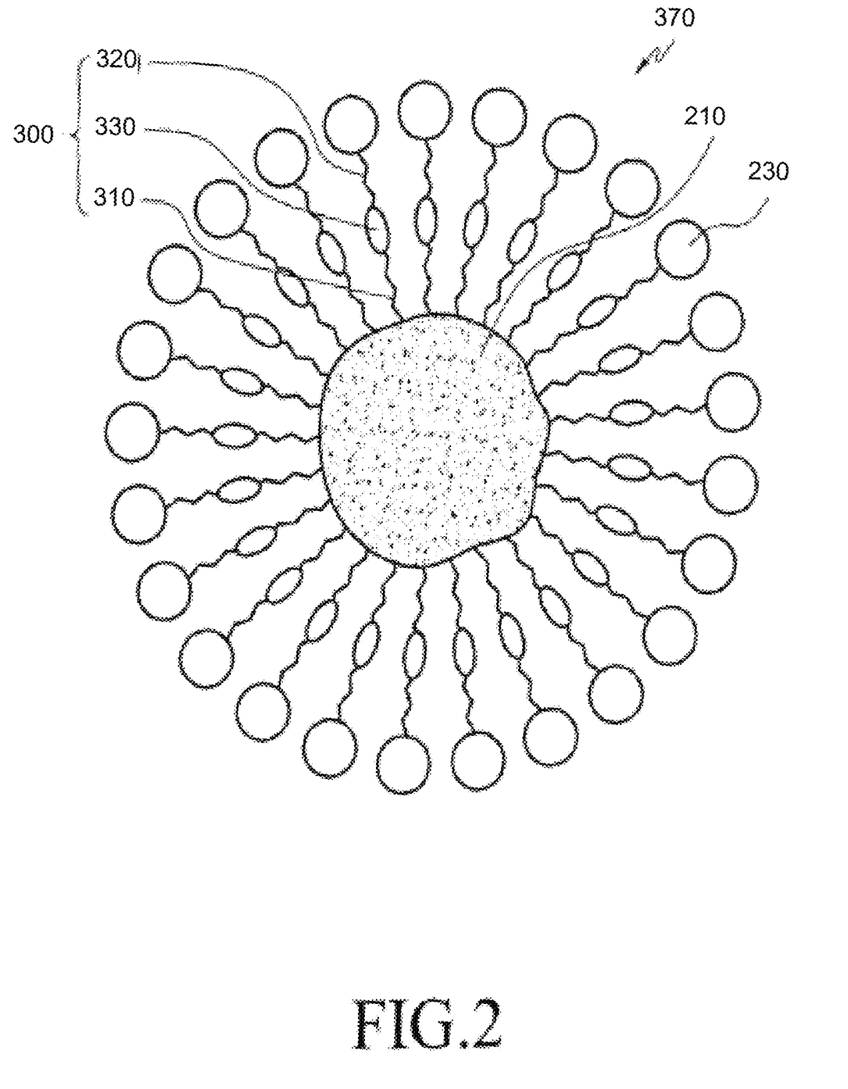
FIG. 2 is an enlarged schematic diagram illustrating a micelle formed by hydrophobic fluid molecules and hydrophilic fluid molecules and surfactant molecules according to an example embodiment of the present disclosure.

For example, with regard to the molecules of a surfactant according to an example embodiment of the present disclosure, hydrophobic functional groups R(Pho) of the molecules are dissolved by the molecules of the hydrophobic fluid 210 and hydrophilic functional groups R(Phi) of the molecules are dissolved by the molecules of the hydrophilic fluid 230. Therefore, the molecules of the surfactant may be, for example, simultaneously combined with the molecules of the hydrophobic fluid 210 and the hydrophilic fluid 230, so as to form a micelle. FIG. 2 is a schematic diagram illustrating a micelle formed by hydrophobic and hydrophilic fluid molecules and surfactant molecules according to an example embodiment of the present disclosure. Referring to FIG. 2, a micelle 370 includes, for example, a hydrophobic fluid 210 and surfactant molecules 300 compactly gathering around the hydrophobic fluid 210. Each surfactant molecule 300 includes, for example, a hydrophobic functional group 310 connected to a molecule of the hydrophobic fluid 210, a hydrophilic functional group 320 connected to a molecule of the hydrophilic fluid 230, and a linker 330 disposed between the hydrophobic functional group 310 and the hydrophilic functional group 320 and interconnecting the hydrophobic functional group 310 and the hydrophilic functional group 320 to each other.

The hydrophobic functional group 310 has a hydrophobic structure. For example, the hydrophobic functional group 310 may have a structure selected from the group consisting of structures of nonpolar straight chain alkyl group, branched-chain alkyl group, branched-chain substituted alkyl group, cyclic substituted alkyl group, and combinations thereof. Those alkyl groups described above may be, for example, a saturated hydrocarbon. Alternatively, for example, in an example embodiment, the alkyl groups described above may be a hydrocarbon including a multiple bond. Also, as an alternative, the hydrophobic functional group 310 may have, for example, a structure similar to the structure of the molecules included in the hydrophobic fluid 210. For example, if the hydrophobic fluid 210 includes alkane molecules, the hydrophobic functional group 310 may be an alkane functional group. For example, if the hydrophobic fluid 210 includes decane molecules, the hydrophobic functional group 310 may be a decane functional group or a functional group of another saturated hydrocarbon having more than ten carbons. It is also noted that the decane molecule, which is hydrophobic, has a structure in which a black dye formed of anthraquinone-based molecules can be dissolved well, and simultaneously has a property that it may be unmixable with a fluid in which ethylene glycol molecules and/or glycerin molecules are mixed.

The hydrophilic functional group 320 has a hydrophilic structure. For example, the hydrophilic functional group 320 may have a structure selected from the group consisting of structures of polar hydroxyl group, carboxyl group, ether group, ester group, amino group, multiple bond of carbon and carbon, and combinations thereof. As an alternative, the hydrophilic functional group 320 may have, for example, a structure similar to the structure of molecules included in the hydrophilic fluid 230. For example, if the hydrophilic fluid 230 includes ethylene glycol molecules, the hydrophilic functional group 320 may be an ethylene glycol functional group. As another alternative, if the hydrophilic fluid 230 includes glycerol molecules, the hydrophilic functional group 320 may be, for example, a glycerol functional group. As another alternative, if the hydrophilic fluid 230 includes glycerol molecules and glycerin molecules mixed with each other, the hydrophilic functional group 320 may be, for example, a functional group including a plurality of ethers. It is noted that the ethylene glycol molecules and the glycerin molecules are connected to neither the hydrophobic fluid 210 nor dye or pigment dissolved or dispersed within the hydrophobic fluid 230.

It is noted that the structural similarity between the hydrophobic functional group 310 and the molecules of the hydrophobic fluid 210 and the structural similarity between the hydrophilic functional group 320 and the molecules of the hydrophilic fluid 230 are beneficial for the respective mixing of the hydrophobic functional group 310 and the hydrophilic functional group 320 with the hydrophobic fluid 210 and the hydrophilic fluid 230 after the step of separating the surfactant molecules 300 into hydrophobic and hydrophilic molecules by a method of manufacturing an electrowetting display device according to the present example embodiment of the present disclosure described below.

The present example embodiment discusses black dyes included in the hydrophobic fluid 210 but example embodiments are not limited thereto. For example, alternatively in an example embodiment, the hydrophobic fluid 210 may include other dyes or pigments of primary colors such as red, green, cyan, magenta, blue, or yellow.

The linker 330 is connected to both the hydrophobic functional group 310 and the hydrophilic functional group 320, so as to indirectly connect the functional groups with each other. Further, the linker 330 includes, for example, a cleavable bond in its structure. The cleavable bond of the linker 330 is broken, for example, when the linker receives energy, such as heat or light, or reacts with another material additionally added thereto. By the breaking of the cleavable bond of the linker 330, the hydrophobic functional group 310 and the hydrophilic functional group 320 connected to the linker 330 are separated from each other, so that the micelle 370 as shown in FIG. 2 may be broken up. As a result and as described in further detail in connection with FIG. 6E, the emulsion may be separated into a separated hydrophobic fluid 213 which includes the hydrophobic functional group 310 of the surfactant molecule 300 mixed with molecules of the hydrophobic fluid 210 and a separated hydrophilic fluid 233 which includes the hydrophilic functional group 320 mixed with molecules of the hydrophilic fluid 230. The separated hydrophobic fluid 213 and the separated hydrophilic fluid 233 do not mix with each other.

Surfactant molecules 300 according to an example embodiment of the present disclosure are designed to enable the bond cleavage or bond breaking to be applied to the linker 330 either selectively or with a first priority, rather than being applied to the hydrophobic functional group 310 or the hydrophilic functional group 320. When the hydrophobic functional group 310 and the hydrophilic functional group 320 include a carbon-carbon (C—C) bond or a carbon-oxygen (C—O) bond, the linker 330 should have, for example, a structure including a bond energy lower than the bond energy of the C—C bond or the C—O bond.

Figure 3:
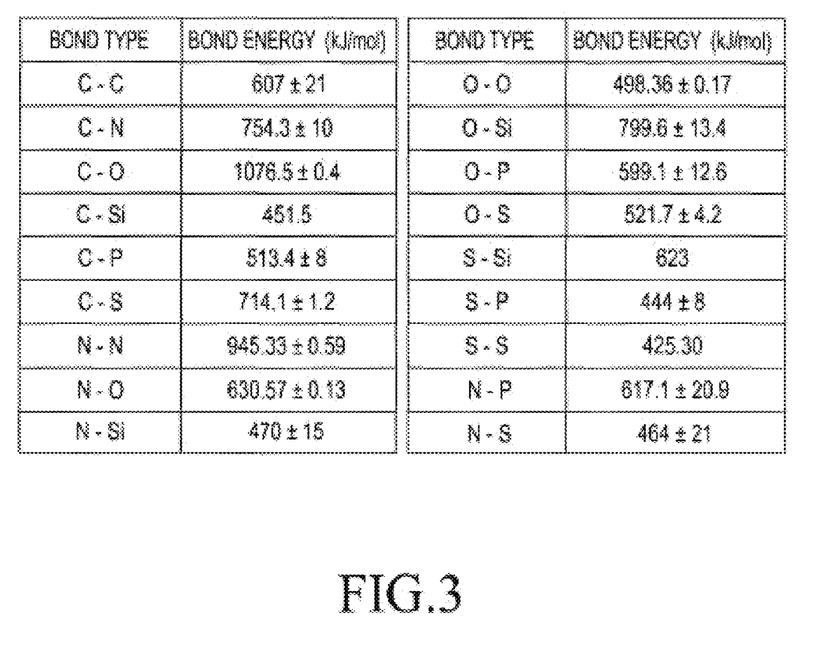
FIG. 3 illustrates a Table showing bond energies of main bonds included in organic compounds.
Figure 4A:
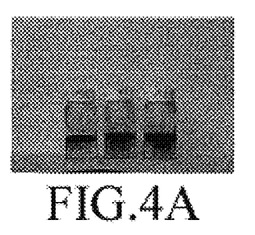
FIGS. 4A to 4F are photographs showing the states in which a surfactant is mixed with a hydrophobic fluid and a hydrophilic fluid so as to form an emulsion.
Figure 4B:
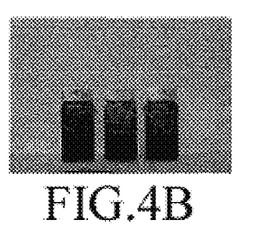
Figure 4C:
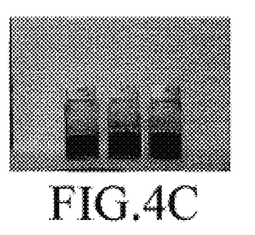
Figure 4D:
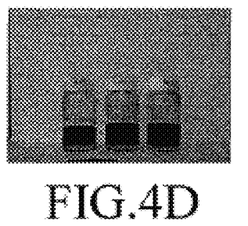
Figure 4E:
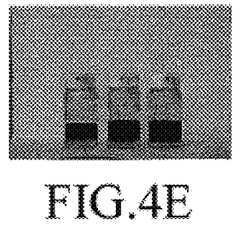
Figure 4F:
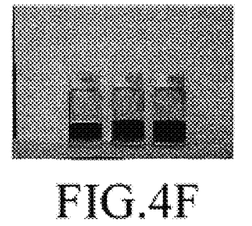

FIG. 3 illustrates a Table showing bond energies of main bonds included in organic compounds. Referring to FIG. 3, the bond energies of the C—C energy or the C—O bond, which are included in the hydrophobic functional group 310 and the hydrophilic functional group 320 and should be broken as little as possible, are higher than, for example, about 600 kJ/mol. Therefore, it is beneficial that the bond energy of the cleavable bond included in the structure of the linker 330 is smaller than about 600 kJ/mol. For example, as bonds of carbon-silicon (C—Si), carbon-phosphor (C—P), nitrogen-silicon (N—Si), nitrogen-sulfur (N—S), oxygen-oxygen (O—O), oxygen-sulfur (O—S), sulfur-phosphorus (S—P), and sulfur-sulfur (S—S) have bond energies which are lower than about 600 kJ/mol, they may be included in the structure of the linker 330.

Among the bonds having low bond energies, the S—S bond can be obtained by, for example, the following reaction formulas set forth below.

[Reaction formula 1]

[Reaction formula 2]

[Reaction formula 3]

The surfactant molecule 300 having an S—S bond as shown in Reaction formula 3 is synthesized from, for example, an alcohol molecule, which is the first starting material as disclosed in Reaction formula 1, and a thiol molecule, which is the second starting material as disclosed in Reaction formula 2. Referring to Reaction formula 1, a hydrogen atom of the alcohol molecule, which is the first starting material and includes a hydrophilic group, is replaced by a tosyl group disclosed in Chemical formula 1 below, so that the alcohol molecule is converted to an alkyl sulfonate molecule as shown in Chemical formula 2. The alkyl sulfonate molecule is converted to a thiol molecule R(Phi)-SH by, for example, a heating reaction. Referring to Reaction formula 2, the thiol molecule R(Pho)-SH, which includes a hydrophobic group R(Pho) and is the second starting material, is mixed with trimethyl amine molecules and dichloro methane molecules and reacts with 2,2'-Dithiodipyridine molecules to become a disulfanyl molecule. Referring to Reaction formula 3, a sulfur atom of the disulfanyl molecule synthesized by Reaction formula 2 is replaced by a sulfur atom of the thiol molecule synthesized by Reaction formula 1. As a result, a disulfur compound, which is a surfactant molecule 300 and includes a linker 330 having a covalent bond of a low bond energy, is synthesized.

[Chemical formula 1]

[Chemical formula 2]

For example, a hydrophobic fluid molecule according to an embodiment of the present disclosure is a decane molecule, which corresponds to a saturated hydrocarbon consisting of ten carbons and having a straight chain structure, and a hydrophilic fluid corresponds to a mixture in which ethylene glycol molecules and glycerin molecules are mixed by a weight ratio of about 2:1. Therefore, based on the fact that functional groups of surfactant molecules 300 are dissolved well when they have structures similar to those of the molecules of the hydrophobic 210 and hydrophilic fluids 230, the hydrophobic functional group 310 dissolved in the hydrophobic fluid 210 may be, for example, a hydrocarbon including at least ten carbons and the hydrophilic functional group 320 dissolved in the hydrophilic fluid 230 may have, for example, a structure in which at least three ethers are connected to each other through carbons between the ethers. Further, based on the fact that the linker 330 of the surfactant molecules 300 has a bond energy lower than about 600 kJ/mol, the surfactant molecules 300 may be a 2-[(Methoxyethoxy)ethoxy]ethyl decyl disulfide disclosed in Chemical formula 3 below. It is noted that the material of Chemical formula 3 can be synthesized by, for example, Reaction formulas 1 to 3 described above.

[Chemical formula 3]

Experiments of mixing fluids and dissolving a surfactant molecule 300 were performed, to examine if a surfactant molecule 300 employing the hydrophobic 310 and hydrophilic 320 functional groups and a linker 330 is converted to an emulsion including micelles 370 when they are mixed with hydrophobic 210 and hydrophilic 230 fluids and if this emulsion is then converted, by, for example, light or heat, to fluids unmixable with each other.

FIGS. 4A to 4F are photographs showing the states in which a surfactant is mixed with a hydrophobic fluid 210 and a hydrophilic fluid 230 so as to form an emulsion. In this experiment, surfactant molecules 300 including S—S bonds having a low bond energy as shown in Chemical formula 3 were used, a fluid in which anthraquinone-based black dye molecules and decane molecules are mixed was used as a hydrophobic fluid 210, and a fluid in which ethylene glycol molecules and glycerol molecules are mixed by a weight ratio of about 2:1 was used as a hydrophilic fluid 230. In the experiment, solutions containing surfactants of different percentages were used. Each solution contained a hydrophilic fluid 230 and a hydrophobic fluid 210 by a weight ratio of about 1:9, and the surfactant occupied about 0 wt %, about 10 wt %, and about 15 wt % of the solutions, respectively.

Referring to FIGS. 4A to 4F, three containers from the left to the right in each photograph contain about 0%, about 10%, and about 15% of surfactants by weight, respectively. FIGS. 4A to 4F sequentially show the states of the containers before, directly after, at about five minutes after, at about ten minutes after, at about thirty minutes after, and at about sixty minutes after the fluids are mixed. As noted from the figures, the quantity of input surfactant is proportional to the time during which the solution is maintained in the emulsion state. Therefore, it is possible to conclude that the disulfide described above has a function of mixing a hydrophilic fluid 230 and a hydrophobic fluid 210 with each other.

Figure 5A:
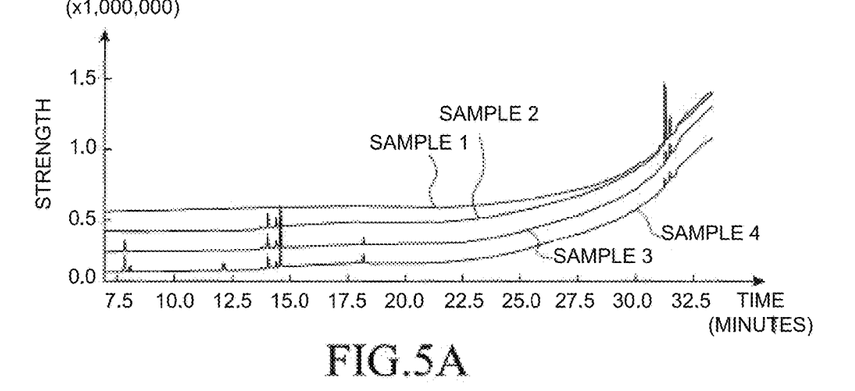
FIGS. 5A and 5B are a Gas Chromatography-Mass Spectroscopy (GC-MS) graph showing measured surfactant components dissolved by ultra-violet rays and a table showing the information of detected materials, respectively.
Figure 5B:
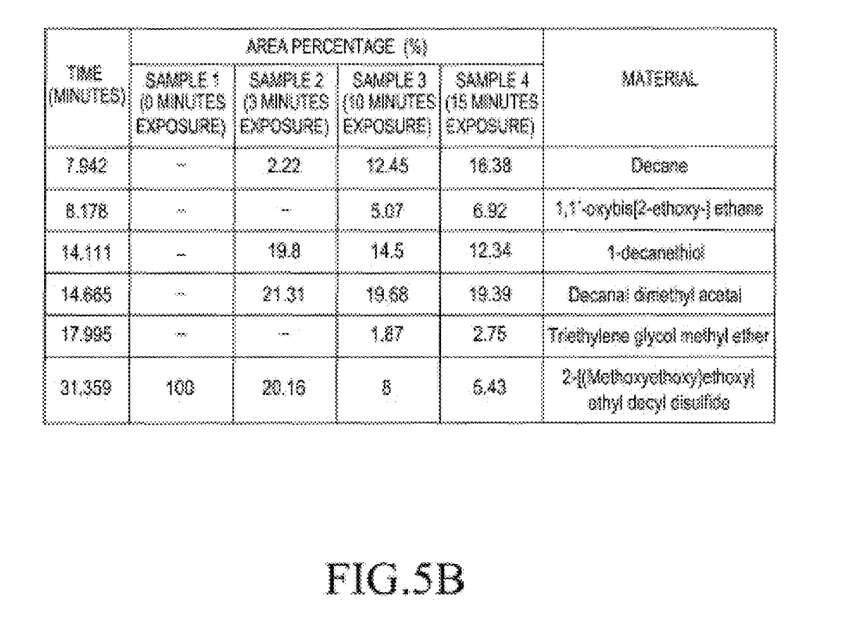

According to an example embodiment of the present disclosure, the cleavable bond included in the linker 330 of the surfactant molecule 300 has a strength weaker and is more easily broken than the bonds included in the hydrophobic 310 and hydrophilic 320 functional groups of the surfactant molecules 300. To confirm this property, the surfactant molecules 300 were dissolved and the structure of the dissolved parts were examined FIGS. 5A and 5B are a Gas Chromatography-Mass Spectroscopy (GC-MS) graph showing measured surfactant components dissolved by ultra-violet rays and a table showing the information of detected materials, respectively. Samples in which methanol and 2-[(Methoxyethoxy)ethoxy]ethyl decyl disulfide as disclosed in Chemical formula 3 were mixed with each other at a mass ratio of about 99:1 were used in the experiments. Further, ultra-violet rays of about 185 nm having an average energy of about 1.318 J/cm$^2$ and ultra-violet rays of about 245 nm having an average energy of about 8.16 J/cm$^2$ were radiated on samples 1 to 4 for about 0 minutes, about 3 minutes, about 10 minutes, and about 15 minutes, respectively.

Referring to FIGS. 5A and 5B, the quantity of surfactant included in each sample was reduced in proportion to the time during which the sample was exposed to the ultraviolet rays. Instead, 1-decanethiol molecules were generated while the S—S bonds included in the linkers 330 of the surfactant molecules 300 were broken. As the time during which the sample was exposed to the ultraviolet rays increased, the 1-decanethiol molecules were increasingly dissolved and some of them were even changed to decane molecules. As the structure of the decane molecule is equal to the structure of the hydrophobic fluid 210, the decane molecules should not act as impurities of the electrowetting display device. The radiation of the ultraviolet rays on the surfactant generated molecules which included molecules derived from the hydrophilic functional groups 320 of the surfactant and had a structure similar to that of the hydrophilic fluid 230 of the electrowetting display device. Therefore, the decane molecules should not act as impurities of the electrowetting display device.

Also, in the process of manufacturing the electrowetting display device, if the quantity of the surfactant is very little in comparison with the entire quantity of the hydrophobic fluid 210 or the hydrophilic fluid 230, a generation of undesired impurities in which the C—C bond or C—O bond of the surfactant molecules 300 are broken may not influence the movement of the fluids included in the completed electrowetting display device.

It is noted that example embodiments of the present disclosure are not limited to using ultraviolet rays to break the cleavable bond included in the linker 330 of the surfactant molecule 300. For example, alternatively, in an example embodiment, ultraviolet rays and heat may be simultaneously applied to the surfactant molecule 300 to break the cleavable bond included in the linker 330 of the surfactant molecule 300. Moreover, alternatively, for example, in an example embodiment, a sound wave energy, such as an ultrasonic wave may be applied to the surfactant molecule 300 to break the cleavable bond included in the linker 330 of the surfactant molecule 300.

Figure 6A:
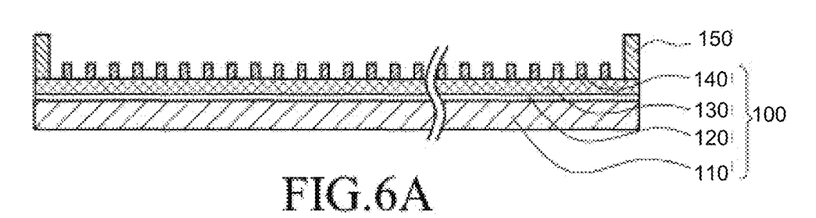
FIGS. 6A to 6F are rough sectional views of a substrate and a fluid mixer for a process of injecting an emulsion into an electrowetting display device and then converting the emulsion into hydrophilic and hydrophobic fluids according to an example embodiment of the present disclosure.

FIGS. 6A to 6F are rough sectional views of a substrate and a fluid mixer for a process of injecting an emulsion into an electrowetting display device and then converting the emulsion into hydrophilic and hydrophobic fluids according to an example embodiment of the present disclosure. Referring to FIG. 6A, which is a rough sectional view of a first substrate of an electrowetting display device according to an example embodiment of the present disclosure, the first substrate 100 includes, for example, a first base substrate 110, a pixel electrode 120, a hydrophobic film 130, and hydrophilic banks 140 as described above with reference to FIGS. 1A and 1B. The first base substrate 110 may be, for example, a flexible substrate or a rigid substrate. For example, the first base substrate 110 may include flexible substrates made of glass, plastic, or a glass fiber reinforced plastic (FRP).

In addition, the pixel electrode 120 may include, for example, a transparent conductive material such as ITO (indium tin oxide), IZO (indium zinc oxide), aluminum zinc oxide (AZO), or cadmium tin oxide (CTO). Alternatively, in an embodiment, the pixel electrode 120 may include, for example, a reflective electric conductor such as aluminum (Al), gold (Au), silver (Ag), copper (Cu), iron (Fe), titanium (Ti), tantalum (Ta), molybdenum (Mo), rubidium (Rb), tungsten (W), and alloys, or combinations thereof.

Moreover, the hydrophobic film 130 may include, for example, amorphous fluoropolymers such as copolymers of tetrafluoroethylene (TFE) and perfluoro-2,2 dimethyl 1,3 dioxide (PDD), sold under the brand name TEFLON® AF 1600 which is a registered trademark of the E.I. DuPont de Nemours and Company Corporation, 101 West 10th St., Wilmington, Del. 19898. Alternatively, other low surface energy polymers such as, for example, parylene may be used to form the hydrophobic film.

The hydrophilic banks 140 may include, for example, a positive photoresist, a negative photoresist, a photoset resin or a thermoset resin.

The first substrate 100 further includes, for example, sealing members 150, which are disposed at edges of the first substrate 100. The sealing members 150 are in contact with a second substrate (not shown), and prevent fluids (not shown) within the display device from leaking out of the display device. It is noted that example embodiments of the present disclosure are not limited to the sealing members 150 being formed at edges of the first substrate 100. Alternatively, for example, in an example embodiment, the sealing members 150 may instead be formed on edges of the second substrate prior to attachment of the second substrate to the first substrate 100 and then the emulsion 380 described in FIG. 6B may be formed between the attached first substrate 100 and the second substrate.

Figure 6B:
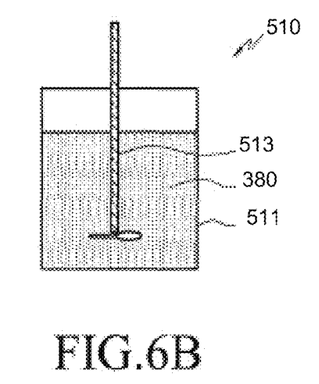

FIG. 6B is a rough sectional view of a fluid mixer 510 in a step in which the emulsion is made. For example, in this step, a hydrophobic fluid, a hydrophilic fluid, and a surfactant are input to a container 511 and are then mixed by a mixing device 513 to become an emulsion 380. For the uniformity of display and brightness of the electrowetting display device, it is possible to use a smaller quantity of hydrophobic fluid 210, which contains, for example, a dye or a pigment expressing the color of a pixel, than the hydrophilic fluid 230. For example, it is possible to use a hydrophobic fluid 210 and a hydrophilic fluid 230 in a weight ratio of about 1:9. As an alternative, it is also possible to use, for example, a larger quantity of hydrophobic fluid 210 than the hydrophilic fluid 230. The surfactant may be input to the fluid mixer 510, for example, either simultaneously with or after the hydrophobic 210 and hydrophilic 230 fluids. It should be noted that undesired elements, such as bubbles, may be formed within the container 511 while the hydrophobic fluid 210 and the hydrophilic fluid 230 are mixed with each other and thus the emulsion forming step may include, for example, an additional sub-step, such as a step of defoamation.

Figure 6C:
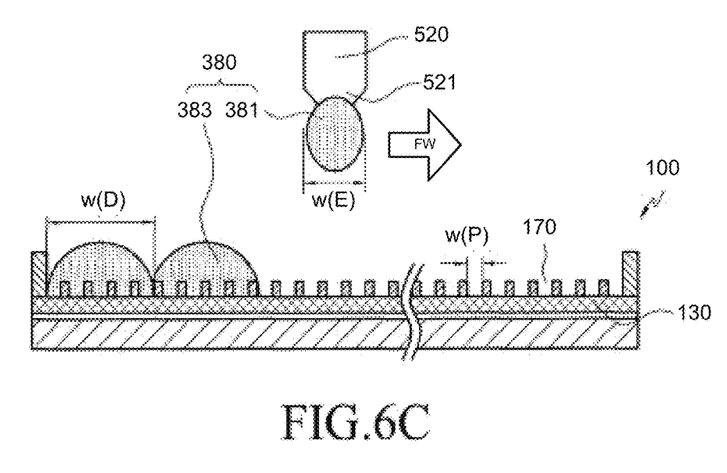

FIG. 6C is a rough sectional view of the first substrate shown in FIG. 6A in a step in which the emulsion shown in FIG. 6B is dispensed onto the first substrate 100. For example, a dispenser 520 for dispensing the previously produced emulsion 380 onto the first substrate 100 is disposed above the first substrate 100. The dispenser 520 can dispense the emulsion 380 onto the first substrate 100 while moving from one end of the first substrate 100 to the other end thereof. As an alternative, the dispenser 520 may include, for example, a plurality of nozzles 521 arranged over the entire surface of the first substrate 100 and can simultaneously dispense the emulsion 380 over the entire surface of the first substrate 100.

The same quantity of hydrophobic fluid 210 should be located within each pixel 170 of the electrowetting display device. If the display device is for displaying a monochrome image, hydrophobic fluids 210 having, for example, dyes or pigments of the same color are located within all pixels 170 of the display device. The emulsion 380 filled in the dispenser 520 corresponds to a fluid in which the hydrophobic fluid 210 is uniformly distributed in the hydrophilic fluid 230. Therefore, when the emulsion 380 is dispensed onto the first substrate 100, even if the dispenser 520 is not aligned with the pixels 170 of the first substrate 100, the same quantity of hydrophobic fluid 210 and the same quantity of hydrophilic fluid 230 can be located in each pixel 170 of the first substrate 100 and a uniform image may be displayed on the display device.

Further, the above-mentioned scheme that does not require the alignment may shorten the working time in dispensing the emulsion 380 on the first substrate 100. To quicken the process, the width w(E) of a droplet 381 dispensed onto the first substrate 100 or the width w(D) of the dispensed emulsion 383 on the first substrate 100 may be, for example, larger than the width w(P) of the pixel 170. The width w(E) of the emulsion droplet 381 corresponds to a width of the emulsion 380 in a direction parallel to the first substrate 100 before being dropped onto the first substrate 100 after being discharged out of the nozzle 521. The width w(D) of the dispensed emulsion 383 on the substrate corresponds to, for example, a width of the emulsion 380 in a direction parallel to the first substrate 100 after being dropped onto the first substrate 100. The width w(P) of the pixel 170 may be, for example, the largest width that can be found in an area such as for example, the area of the pixel electrode 120 at which the emulsion 380 is to be located. For example, the width w(P) of the pixel 170 may have a value within a range from about 500 μm to about 700 μm and the width of the emulsion droplet 381 of the emulsion 380 or the width of the dispensed emulsion 383 may be larger than about 700 μm. If the emulsion droplet 381 is too large, an excessively large weight of the emulsion 380 may cause physical damage to the hydrophobic film 130. Therefore, the emulsion droplet 381 should have a width which is, for example, not larger than about ten times of the width w(P) of the pixel 170.

After the emulsion 380 is dispensed onto the first substrate 100 and is then separated into the hydrophobic fluid and the hydrophilic fluid, the second substrate (not shown) is attached to the first substrate 100. In consideration of this step, it may be beneficial that the dispensed emulsions 383 on the first substrate 100 are adjacent to each other and are not spaced apart from each other. Referring to FIG. 6C, to make the emulsion 380 be uniformly distributed on the first substrate 100, a portion of one dispensed emulsion 383 may be in contact with or overlap a portion of an adjacent dispensed emulsion 383. If the dispensed emulsions 383 on the first substrate 100 are small, the number of the dispensed emulsions 383 in a unit area of the first substrate 100 may become large and may thus require a longer time for the emulsion dispensing step as shown in FIG. 6C. The width of the dispensed emulsion 383 may be, for example, at least about three times the width w(P) of the pixel 170.

As an alternative, although not shown, the width of the emulsion droplet of the emulsion may be, for example, smaller than the width of one pixel. For example, the emulsion may be dispensed onto the substrate in such a manner that emulsion droplets (minute emulsion droplets) of several μm may be collected in one pixel. In this event, the width of the minute emulsion droplets may be, for example, narrower than the width of the unit pixel. The width of the unit pixel may be, for example, the narrowest width that can be found in the area at which the emulsion is to be located. For example, the width of the minute emulsion droplets may have a value within a range from about 1.5 μm to about 100 μm and a plurality of emulsion droplets may be dispensed into one pixel by an inkjet equipment. These minute emulsion droplets are available when hydrophobic fluids including dyes or pigments of different colors are dispensed into adjacent pixels (for example, in a color display device), respectively. In addition, these minute emulsion droplets may also be used for an electrowetting display device (for example, in a monochrome display device) in which adjacent pixels display the same color.

Figure 6D:
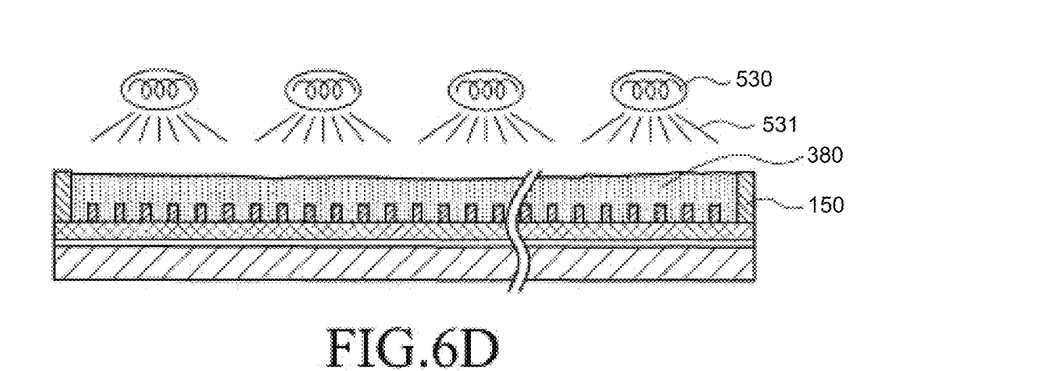

FIG. 6D is a rough sectional view of the substrate after the emulsion dispensing step as shown in FIG. 6C is completed. The emulsion 380 is filled between the sealing members 150 located at opposite ends of the first substrate 100 and ultraviolet rays 531 are radiated onto the emulsion 380 from an ultraviolet ray source 530 spaced apart from the emulsion 380.

As described above, the linker 330 included in the surfactant molecule 300 included in the emulsion 380 has a bond energy lower than the bond energy of the bonds included in the hydrophobic functional groups 310 and/or hydrophilic functional groups 320. Therefore, the radiation of the ultraviolet rays 531 onto the emulsion 380 may break the bonds included in the linkers 330 of the surfactant molecules 300, may reduce the quantity of the micelles included in the emulsion 380, and may change the emulsion 380 into a separated hydrophilic fluid 233 and a separated hydrophobic fluid 213 which are unmixable with each other as will be described in further detail in connection with FIG. 6E. In this event, excessive radiation of the ultraviolet rays in view of the intensity or time of the radiation may break not only the bonds of the linkers 330 but also the bonds of the hydrophilic 320 or hydrophobic 310 functional groups. Therefore, it may be necessary to control the time and intensity of the radiation of the ultraviolet rays 531. The above description discusses radiation of the ultraviolet ray source 530 onto the emulsion 380. However, as an alternative, to dissolve the linkers of the surfactant molecules 300, it is possible to apply, for example, heat to the first substrate 100 containing the emulsion 380 thereon. Otherwise, it is also possible to, for example, either simultaneously provide the ultraviolet ray energy and the heat energy or provide a sound wave energy, such as an ultrasonic wave to the first substrate 100 containing the emulsion 380 thereon.

FIG. 6D shows a state in which the ultraviolet rays 531 are radiated onto the first substrate 100 on which the second substrate (not shown) is not assembled. However, for example, as an alternative, after the first substrate 100 and the second substrate are attached to each other, the ultraviolet rays 531 may be radiated toward the attached first substrate 100 and second substrate from the outside of the attached first substrate 100 and second substrate. For example, after the first substrate 100 on which the emulsion 380 has been dispensed is attached to the second substrate, the ultraviolet rays 531 may be radiated from above the second substrate. As an alternative, for example, after the first substrate 100 and the second substrate are attached to each other, an emulsion may be injected into the space between the attached first substrate 100 and second substrate through a corner of the attached first substrate 100 and second substrates by a proper method, such as, for example, a vacuum injection, and the ultraviolet rays 531 may be then radiated from above the second substrate.

Figure 6E:
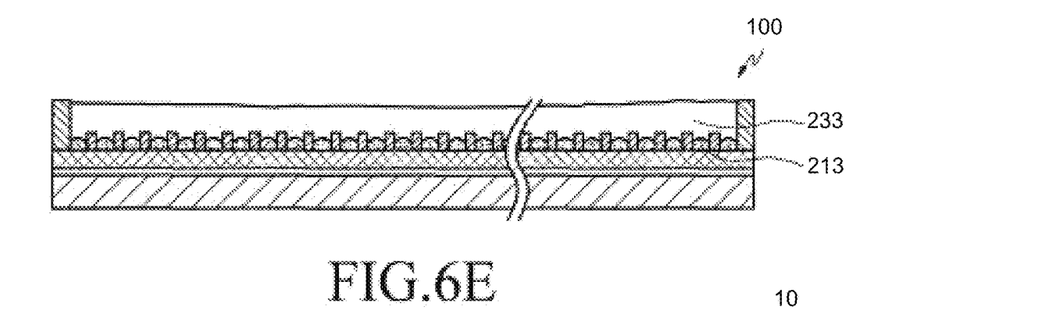

FIG. 6E is a rough sectional view of the first substrate 100 in which the emulsion 380 has been separated into a separated hydrophobic fluid 213 and a separated hydrophilic fluid 233 by the ultraviolet ray radiating step shown in FIG. 6D. The separated hydrophobic fluid 213 includes the hydrophobic functional groups 310 of the surfactant molecules 300 mixed with molecules of the original hydrophobic fluid 210, and the separated hydrophilic fluid 233 includes the hydrophilic functional groups 320 of the surfactant molecules 300 mixed with molecules of the original hydrophilic fluid 230. The separated hydrophobic fluid 213 and the separated hydrophilic fluid 233 do not mix with each other.

When a linker 330 of a surfactant molecule 300 has an S—S bond, the hydrophobic 310 and hydrophilic 320 functional groups of the surfactant molecules 300 may be changed to thiol molecules. Therefore, at least one of the separated hydrophobic fluid 213 and the separated hydrophilic fluid 233 as shown in FIG. 6E may include thiol molecules. As an alternative, for example, a linker 330 of a surfactant molecule 300 may have a bond having a bond energy lower than the bond energy of the C—C or C—O bond wherein the bond of the linker 330 may be a bond including one of Si—C, C—P, N—Si, N—S, O—S, or S—P, which may be broken by ultraviolet rays, heat, or catalyst. In this alternative, the separated hydrophilic fluid 233 or the separated hydrophobic fluid 213 may include, for example, an element included in the bond of the linker 330 of the surfactant molecule 300 broken by ultraviolet rays, heat, or catalyst as described above.

Figure 6F:
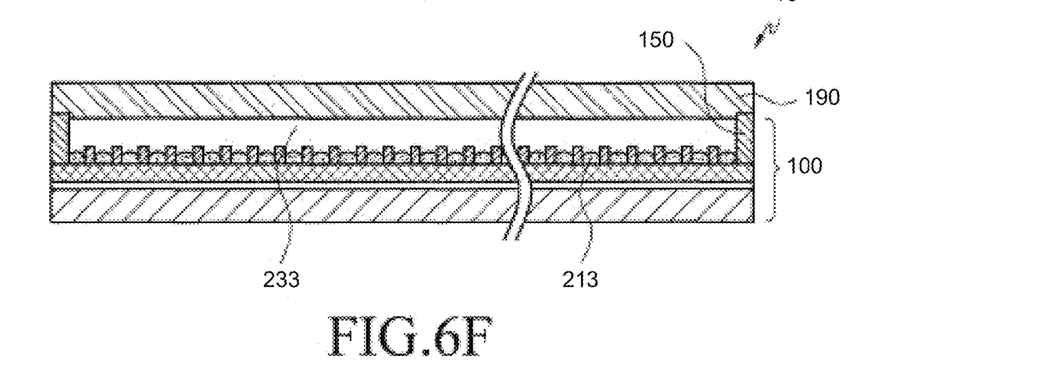

FIG. 6F is a sectional view of an electrowetting display device 10 in which the second substrate 190 has been attached to the first substrate 100 as shown in FIG. 6E. The second substrate 190 is attached to, for example, the sealing members 150 disposed at the edges of the first substrate 100 and prevents the separated hydrophobic and hydrophilic fluids 213 and 233 from leaking out of the display device 10. The second substrate 190 may be, for example, a flexible substrate or a rigid substrate. For example, the second substrate 190 may include flexible substrates made of glass, plastic, or a glass fiber reinforced plastic (FRP).

In the present example embodiment, the sealing members 150 are formed on the first substrate 100 prior to attaching the second substrate 190 to the first substrate 100 but example embodiments of the present disclosure are not limited thereto. For example, alternatively, in an example embodiment, the sealing members 150 may be disposed on edges of the second substrate 190 and then the second substrate 190 having sealing members formed thereon may be attached to the first substrate 100 and the emulsion 380 is then formed between the attached first and second substrates 100, 190.

Having described example embodiments of the present disclosure, it is further noted that it is readily apparent to those of ordinary skill in the art that various modifications may be made without departing from the spirit and scope of the disclosure which is defined by the metes and bounds of the appended claims.

What is claimed is:

1. An emulsion comprising:
a hydrophilic fluid;
a hydrophobic fluid; and
a cleavable surfactant with the general formula:

$R^1$-L-$R^2$ wherein:
L is a linker having a cleavable bond comprising a disulfide;
$R^1$ is a hydrophobic functional group having the general formula $CH_3$—$(CH_2)_n$ and n=4 to 10; and
$R^2$ is a hydrophilic functional group having the general formula $R_{n'}$—$CH_3$ wherein R=($CH_2$—$CH_2$—O)— and n'=2 to 4.

2. The emulsion of claim 1, wherein the hydrophobic fluid includes a saturated hydrocarbon having at least ten carbon atoms and the hydrophilic fluid includes ethylene glycol and glycerin.

3. The emulsion of claim 2, wherein a weight ratio of an amount of ethylene glycol in the hydrophilic fluid to an amount of glycerol in the hydrophilic fluid is about 2:1.

4. The emulsion of claim 1, wherein the hydrophilic fluid and the hydrophobic fluid form a solution having a weight ratio of about 1:9 and an amount of the surfactant is substantially less than or equal to about 15 wt. % of the solution.

5. The emulsion of claim 1, further comprising a dye.

6. The emulsion of claim 1, wherein the cleavable surfactant is a 2-[(Methoxyethoxy)ethoxy]ethyl decyl disulfide.

* * * * *

UNITED STATES PATENT AND TRADEMARK OFFICE
CERTIFICATE OF CORRECTION

PATENT NO. : 10,011,102 B2
APPLICATION NO. : 14/507588
DATED : July 3, 2018
INVENTOR(S) : Jo et al.

Page 1 of 1

It is certified that error appears in the above-identified patent and that said Letters Patent is hereby corrected as shown below:

In the Claims

In Column 16, Line 49, in Claim 1, delete "$R_{n'}$—$CH_{3\ wherein}$" and insert -- $R_{n'}$—$CH_3$ wherein --, therefor.

Signed and Sealed this
Thirtieth Day of April, 2019

Andrei Iancu
*Director of the United States Patent and Trademark Office*